(12) United States Patent
Turco et al.

(10) Patent No.: US 10,889,644 B2
(45) Date of Patent: Jan. 12, 2021

(54) HUMANIZED ANTI-BAG3 ANTIBODIES

(71) Applicant: BIOUNIVERSA S.R.L., Montoro (IT)

(72) Inventors: Maria Caterina Turco, Avellino (IT); Alessandra Rosati, Baronissi (IT); Vincenzo De Laurenzi, Pescara (IT); Gianluca Sala, Pescara (IT)

(73) Assignee: BIOUNIVERSA S.R.L., Montoro (IT)

( * ) Notice: Subject to any disclaimer, the term of this patent is extended or adjusted under 35 U.S.C. 154(b) by 199 days.

(21) Appl. No.: 15/770,690

(22) PCT Filed: Nov. 2, 2016

(86) PCT No.: PCT/EP2016/076384
§ 371 (c)(1),
(2) Date: Apr. 24, 2018

(87) PCT Pub. No.: WO2017/076878
PCT Pub. Date: May 11, 2017

(65) Prior Publication Data
US 2019/0153090 A1 May 23, 2019

(30) Foreign Application Priority Data
Nov. 5, 2015 (IT) .............................. UB2015A5097

(51) Int. Cl.
| | | |
|---|---|---|
| *C07K 16/28* | (2006.01) | |
| *C07K 16/18* | (2006.01) | |
| *C07K 16/30* | (2006.01) | |
| *A61P 35/00* | (2006.01) | |
| *A61K 9/00* | (2006.01) | |
| *A61K 39/395* | (2006.01) | |
| *A61K 45/06* | (2006.01) | |
| *A61K 39/00* | (2006.01) | |

(52) U.S. Cl.
CPC ............ *C07K 16/28* (2013.01); *A61K 9/0014* (2013.01); *A61K 9/0029* (2013.01); *A61K 9/0053* (2013.01); *A61K 39/3955* (2013.01); *A61K 45/06* (2013.01); *A61P 35/00* (2018.01); *C07K 16/18* (2013.01); *C07K 16/30* (2013.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
CPC ...................................................... C07K 16/28
USPC ...................................................... 424/133.1
See application file for complete search history.

(56) References Cited

U.S. PATENT DOCUMENTS 7,807,788 B2 * 10/2010 Ashman ............... C07K 16/244
530/387.1

FOREIGN PATENT DOCUMENTS

| EP | 0239400 B1 | 8/1994 |
|---|---|---|
| WO | 89/09622 A1 | 10/1989 |
| WO | 90/07861 A1 | 7/1990 |
| WO | 03/055908 A2 | 7/2003 |
| WO | 2011/067377 A1 | 6/2011 |
| WO | 2014/147503 A2 | 9/2014 |

OTHER PUBLICATIONS

Ammirantea, et al., "IKKγ protein is a target of BAG3 regulatory activity in human tumor growth", PNAS vol. 107 No. 16, Apr. 20, 2010, pp. 7497-7502.
Clackson, et al., "Making antibody fragments using phage display libraries", Nature vol. 352, Aug. 15, 1991, pp. 624-628.
Festa, et al., "BAG3 Protein Is Overexpressed in Human Glioblastoma and Is a Potential Target for Therapy", The American Journal of Pathology, vol. 178, No. 6, Jun. 2011, pp. 2504-2512.
Franceschelli, et al., "bag3 Gene Expression Is Regulated by Heat Shock Factor 1", Journal of Cellular Physiology, vol. 215, Issue 3, Jun. 2008, pp. 575-577.
Kalluri, "The biology and function of fibroblasts in cancer", Nature Reviews Cancer, vol. 16, Sep. 2016, pp. 582-598.
Kettleborough, et al., "Humanization of a mouse monoclonal antibody by CDR-grafting: the importance of framework residues on loop conformation", Protein Engineering vol. 4 No. 7, Oct. 1991, pp. 773-783.
Köhler, et al., "Continuous cultures of fused cells secreting antibody of predefined specificity", Nature, vol. 256, Aug. 7, 1975, pp. 495-497.
Rosati, et al., "BAG3 promotes pancreatic ductal adenocarcinoma growth by activating stromal macrophages", Nature Communications, vol. 6, Nov. 2, 2015, pp. 1-11.
Rosati, et al., "BAG3: a multifaceted protein that regulates major cell pathways", Cell Death and Disease (2011) 2, e141, Apr. 2011, pp. 1-6.
Rosati, et al., "Expression of the Antiapoptotic Protein BAG3 Is a Feature of Pancreatic Adenocarcinoma and Its Overexpression Is Associated With Poorer Survival", The American Journal of Pathology, vol. 181, No. 5, Nov. 2012, pp. 1524-1529.
Wang, et al., "Characterization of BAG3 cleavage during apoptosis of pancreatic cancer cells", Journal of Cellular Physiology, vol. 224 No. 1, Jul. 2010, pp. 94-100.
International Search Report dated Feb. 2, 2017 in International Application No. PCT/EP2016/076384.
Italian Search Report dated Jul. 1, 2016 in Italian Application No. IT UB20155097.

* cited by examiner

*Primary Examiner* — Sean E Aeder
(74) *Attorney, Agent, or Firm* — Perkins Coie LLP

(57) ABSTRACT

The present invention provides for a humanized anti-BAG3 antibody or a fragment thereof, pharmaceutical compositions comprising said antibody and its use as a medicament, in particular for use in the treatment of pancreatic tumours or other pathologies of an immune, inflammatory, neoplastic, cardiovascular and/or degenerative nature.

20 Claims, 6 Drawing Sheets
Specification includes a Sequence Listing.

Figure 1. ELISA showing the screening for antibody binding activity with a coating using Peptide 2 (BAG3 fragment).
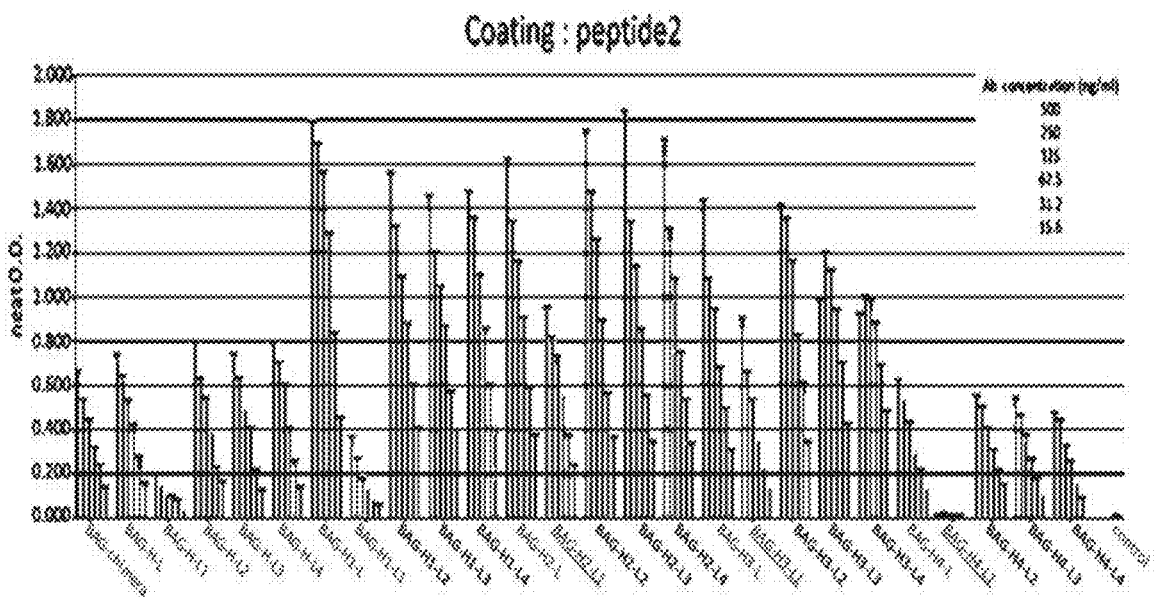
In bold are indicated antibodies chosen for further analysis.

Figure 2. ELISA showing the screening for antibody binding activity with a coating using recombinant full length BAG3 protein.
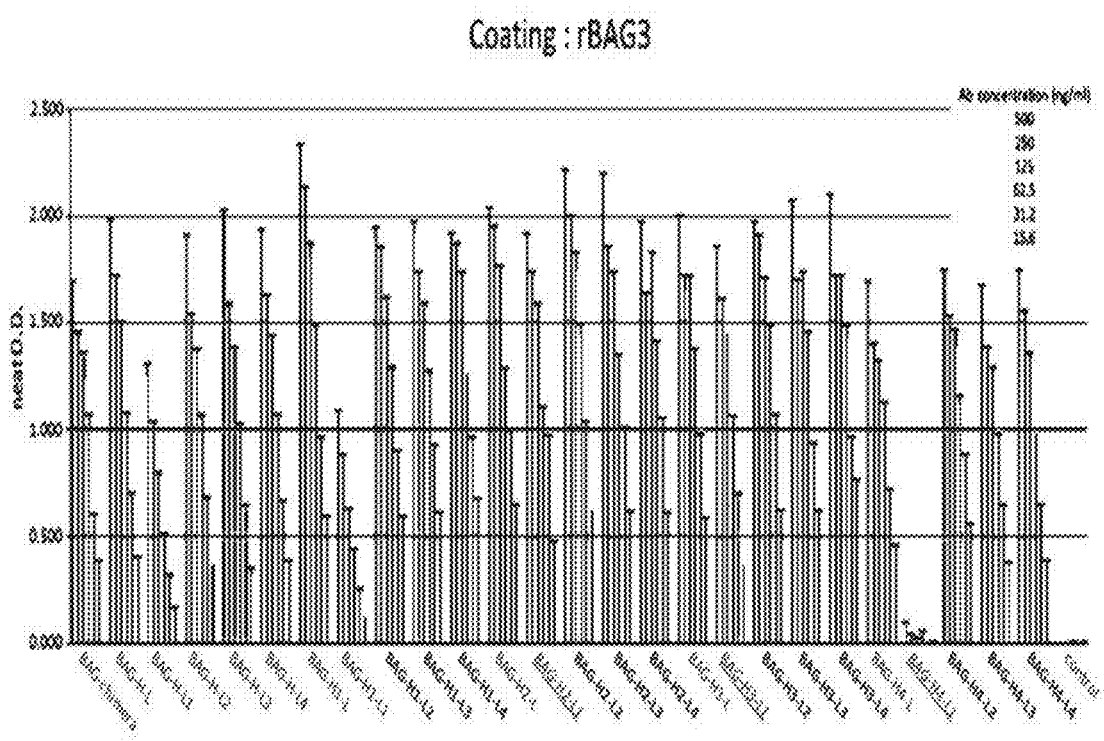
In bold are indicated antibodies chosen for further analysis.

Figure 3. Flow cytometric evaluation of the ability of the antibody variants to block BAG3 binding to macrophage surface Numbers above the columns indicate KD for the indicated antibody.

Figure 4. Effect of humanized AC-2 antibody variants on tumor growth *in vivo*
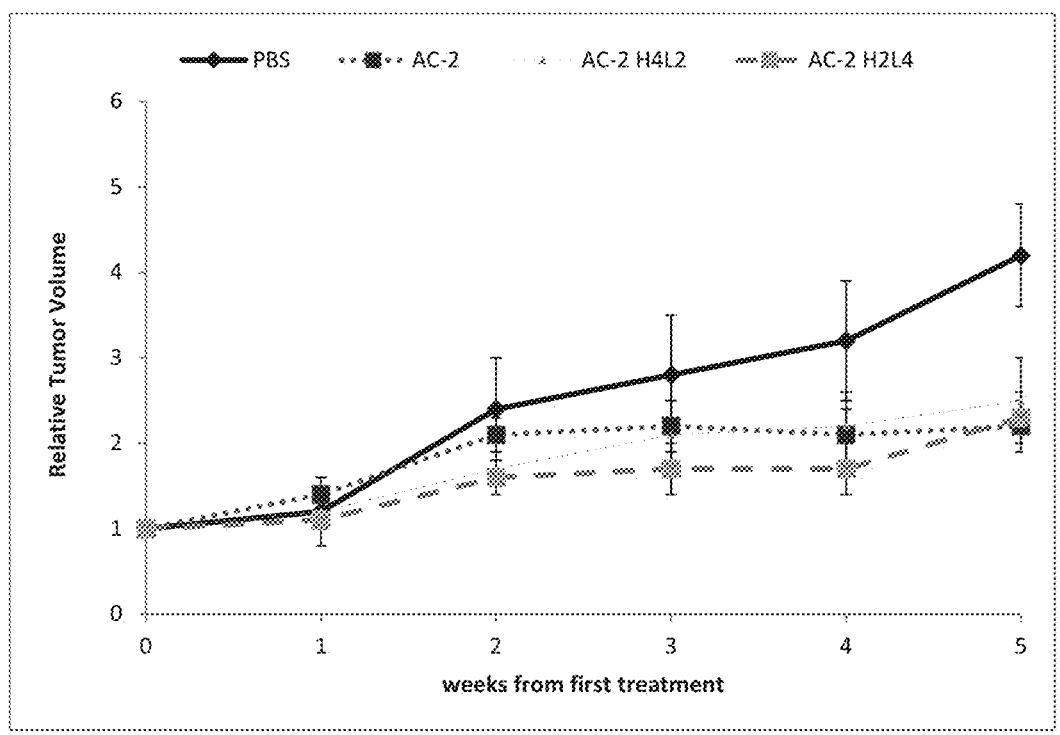

Figure 5. Effect of humanized AC-2 antibody variant H2L4 on activated fibroblasts within the tumor mass.
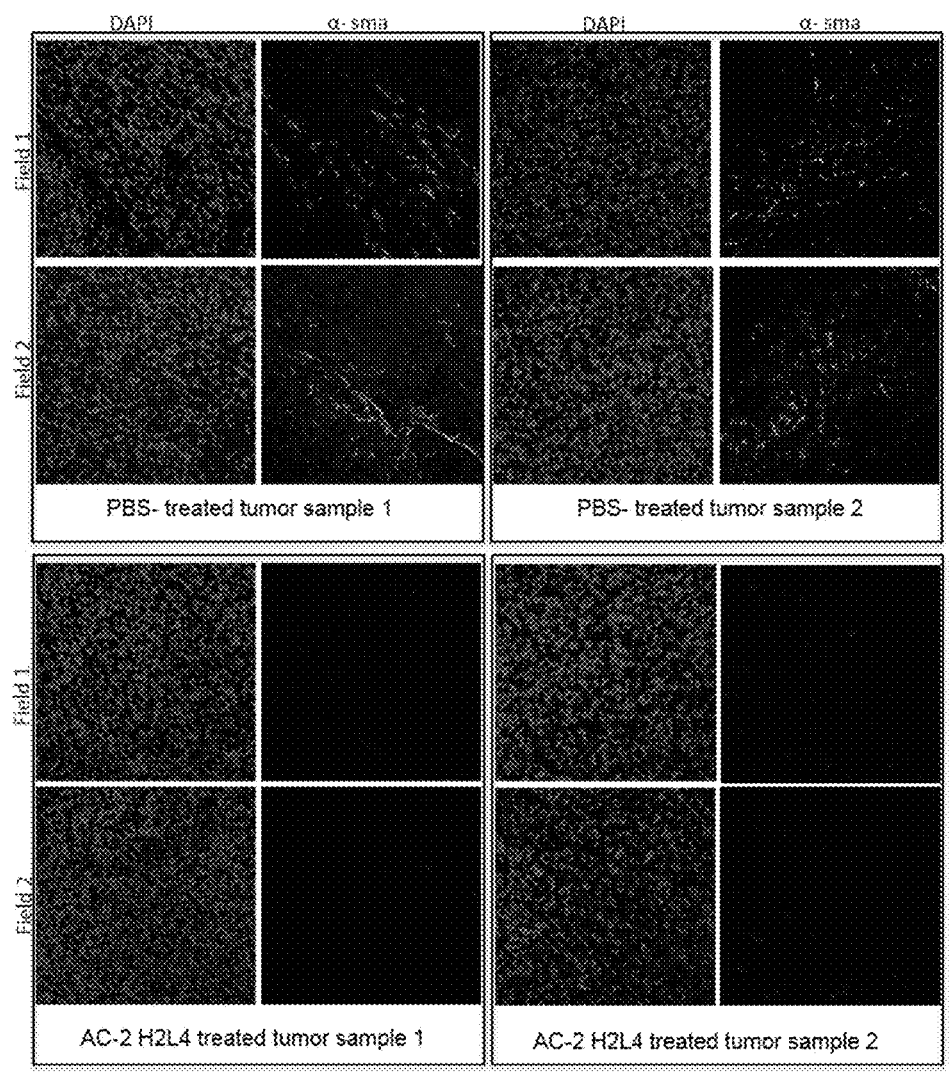

Figure 6. Quantification of the AC-2 H2L4 effect on activated fibroblasts number.
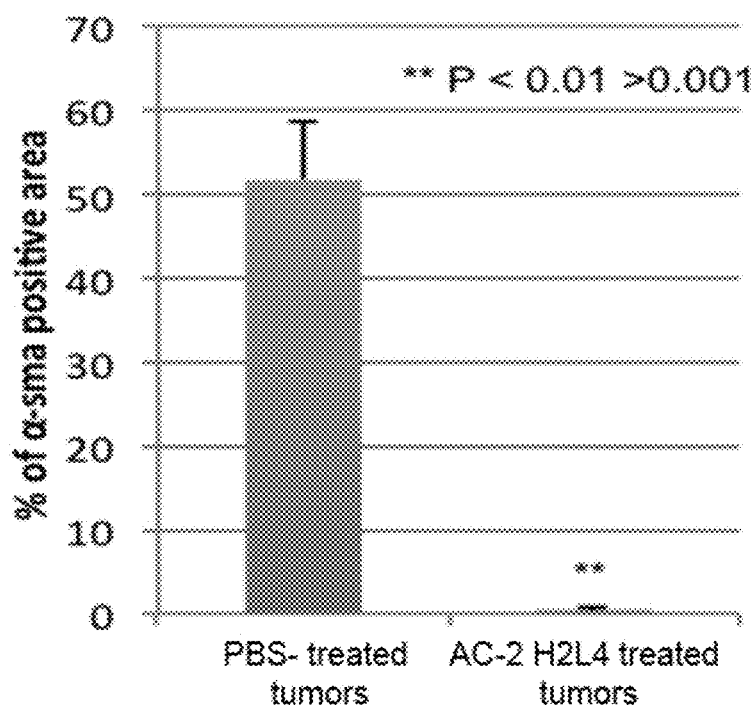

SEQUENCE LISTING

```
<160> NUMBER OF SEQ ID NOS: 26

<210> SEQ ID NO 1
<211> LENGTH: 115
<212> TYPE: PRT
<213> ORGANISM: Mus musculus

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Gly Val Asp Pro Ala Asn Gly Asn Thr Arg Tyr Asp Pro Lys Phe
    50                  55                  60
```

```
Gln Gly Lys Ala Thr Leu Thr Ala Asp Thr Ser Ser Thr Ala Tyr
 65                  70                  75                  80

Leu Gln Leu Ser Ser Leu Thr Ser Glu Asp Thr Ala Val Tyr Tyr Cys
                 85                  90                  95

Gly Arg Asp Gly Ala Met Asp Tyr Trp Gly Gln Gly Thr Ser Val Thr
            100                 105                 110

Val Ser Ser
        115

<210> SEQ ID NO 2
<211> LENGTH: 113
<212> TYPE: PRT
<213> ORGANISM: Mus musculus

<400> SEQUENCE: 2

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp His Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                 70                  75                  80

Ile Ser Ser Val Lys Ala Glu Asp Leu Ala Ile Tyr Tyr Cys Gln Gln
                85                  90                  95

Tyr Tyr Thr Tyr Pro Leu Thr Phe Gly Ala Gly Thr Lys Leu Glu Leu
            100                 105                 110

Lys

<210> SEQ ID NO 3
<211> LENGTH: 10
<212> TYPE: PRT
<213> ORGANISM: Mus musculus

<400> SEQUENCE: 3

Gly Phe Asn Ile Lys Asp Thr Tyr Met Tyr
1               5                   10

<210> SEQ ID NO 4
<211> LENGTH: 17
<212> TYPE: PRT
<213> ORGANISM: Mus musculus

<400> SEQUENCE: 4

Gly Val Asp Pro Ala Asn Gly Asn Thr Arg Tyr Asp Pro Lys Phe Gln
1               5                   10                  15

Gly

<210> SEQ ID NO 5
<211> LENGTH: 6
<212> TYPE: PRT
<213> ORGANISM: Mus musculus

<400> SEQUENCE: 5

Asp Gly Ala Met Asp Tyr
1               5
```

```
<210> SEQ ID NO 6
<211> LENGTH: 17
<212> TYPE: PRT
<213> ORGANISM: Mus musculus

<400> SEQUENCE: 6

Lys Ser Ser Gln Ser Leu Leu Tyr Ser Ser Asn Gln Lys Asn Tyr Leu
1               5                   10                  15
Ala

<210> SEQ ID NO 7
<211> LENGTH: 7
<212> TYPE: PRT
<213> ORGANISM: Mus musculus

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Mus musculus

<400> SEQUENCE: 8

Gln Gln Tyr Tyr Thr Tyr Pro Leu Thr
1               5

<210> SEQ ID NO 9
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="genomic DNA"
      /organism="Mus musculus"

<400> SEQUENCE: 9
gaggtccagc tgcagcagag cggtgccgaa ctggtgaagc caggagcatc cgtcaaactg     60
tcttgtacag catccgggtt taacattaag gacacctaca tgtattgggt gaaacagagg    120
ccagagcagg gcctggaatg gatcggcgga gtggaccccg ctaacgggaa tacacgatac    180
gatcctaagt tccagggaaa agccaccctg acagctgaca cttccagctc taccgcatat    240
ctgcaactga gttccctgac atctgaggat actgccgtgt actattgcgg gagggatggg    300
gctatggact actggggtca ggggacttcc gtcactgtct cgagc                    345

<210> SEQ ID NO 10
<211> LENGTH: 339
<212> TYPE: DNA
<213> ORGANISM: Mus musculus
<220> FEATURE:
<221> NAME/KEY: source
<222> LOCATION: 1..339
<223> OTHER INFORMATION: /mol_type="genomic DNA"
      /organism="Mus musculus"

<400> SEQUENCE: 10
gatattgtga tgtctcagtc cccaagcagc ctggcagtct cagtcggcga aaaggtgacc     60
atgtcctgta atcctctca gtccctgctg tactccagca accagaagaa ttatctggca    120
tggcaccagc agaagcccgg acagagtcct aaactgctga tctactgggc agcacaagg    180 gagtctggcg tgccagaccg gttcactggc tcaggctccg ggaccgattt taccctgaca    240
```

```
atctctagtg tcaaagccga agacctggct atctactatt gccagcagta ttacacttat      300
cctctgacat ttggagcagg gactaaactg gaactgaag                             339
```

<210> SEQ ID NO 11
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="other DNA"
      /organism="Homo sapiens"

<400> SEQUENCE: 11

```
gcggccgcca tgaattttgg actgaggctg attttcctgg tgctgaccct gaaaggcgtc       60
cagtgtcagg tgcagctggt ccagagcggg gcagaggtga agaaaccagg tgccagcgtg      120
aaggtctctt gcaaagccag tggcttcaac atcaaggaca catacatgta ttgggtgcga      180
caggcccctg gccagggtct ggaatggatg ggcggcgtga ccccgcaaa tggaaatact       240 agatacgatc ctaaatttca gggaaggggtg accatgacac gggacacttc aacctcgacg      300
gtctatatgg agctgtccag cctgagatcc gaagatacag ccgtgtacta ttgtgcccgc      360
gacggggcta tggattactg gggccaggga actctggtga ccgtctcgag cgctagcaca      420
aagggcccta gtgtgtttcc tctggctccc tcttccaaat ccacttctgg tggcactgct      480
gctctgggat gcctggtgaa ggattacttt cctgaacctg tgactgtctc atggaactct      540
ggtgctctga cttctggtgt ccacactttc cctgctgtgc tgcagtctag tggactgtac      600
tctctgtcat ctgtggtcac tgtgccctct tcatctctgg aacccagac ctacatttgt       660 aatgtgaacc acaaaccatc caacactaaa gtggacaaaa agtggaacc caaatcctgt       720 gacaaaaccc acacctgccc accttgtcct gcccctgaac tgctgggagg accttctgtg      780
tttctgttcc cccccaaacc aaaggatacc ctgatgatct ctagaacccc tgaggtgaca      840
tgtgtggtgg tggatgtgtc tcatgaggac cctgaggtca aattcaactg gtacgtggat      900
ggagtggaag tccacaatgc caaaaccaag cctagagagg aacagtacaa ttcaacctac      960
agagtggtca gtgtgctgac tgtgctgcat caggattggc tgaatggcaa ggaatacaag     1020
tgtaaagtct caaacaaggc cctgcctgct ccaattgaga aaacaatctc aaaggccaag     1080
ggacagccta gggaacccca ggtctacacc ctgccaccctt caagagagga atgaccaaa     1140 aaccaggtgt ccctgacatg cctggtcaaa ggcttctacc cttctgacat tgctgtggag     1200
tgggagtcaa atggacagcc tgagaacaac tacaaaacaa ccccccctgt gctggattct     1260
gatggctctt tctttctgta ctccaaactg actgtggaca gtctagatg gcagcagggg      1320 aatgtctttt cttgctctgt catgcatgag gctctgcata accactacac tcagaaatcc     1380
ctgtctctgt ctcccgggaa atgatagtaa aagctt                               1416
```

<210> SEQ ID NO 12
<211> LENGTH: 445
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30
```

```
Tyr Met Tyr Trp Val Arg Gln Ala Pro Gly Gln Gly Leu Glu Trp Met
         35                  40                  45
Gly Gly Val Asp Pro Ala Asn Gly Asn Thr Arg Tyr Asp Pro Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Asp Gly Ala Met Asp Tyr Trp Gly Gln Gly Thr Leu Val Thr
             100                 105                 110
Val Ser Ser Ala Ser Thr Lys Gly Pro Ser Val Phe Pro Leu Ala Pro
         115                 120                 125
Ser Ser Lys Ser Thr Ser Gly Gly Thr Ala Ala Leu Gly Cys Leu Val
         130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                 165                 170                 175
Leu Tyr Ser Leu Ser Ser Val Val Thr Val Pro Ser Ser Ser Leu Gly
             180                 185                 190
Thr Gln Thr Tyr Ile Cys Asn Val Asn His Lys Pro Ser Asn Thr Lys
         195                 200                 205
Val Asp Lys Lys Val Glu Pro Lys Ser Cys Asp Lys Thr His Thr Cys
         210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                 245                 250                 255
Val Thr Cys Val Val Val Asp Val Ser His Glu Asp Pro Glu Val Lys
             260                 265                 270
Phe Asn Trp Tyr Val Asp Gly Val Glu Val His Asn Ala Lys Thr Lys
         275                 280                 285
Pro Arg Glu Glu Gln Tyr Asn Ser Thr Tyr Arg Val Val Ser Val Leu
         290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                 325                 330                 335
Ala Lys Gly Gln Pro Arg Glu Pro Gln Val Tyr Thr Leu Pro Pro Ser
             340                 345                 350
Arg Glu Glu Met Thr Lys Asn Gln Val Ser Leu Thr Cys Leu Val Lys
         355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                 405                 410                 415
Gln Gly Asn Val Phe Ser Cys Ser Val Met His Glu Ala Leu His Asn
             420                 425                 430
His Tyr Thr Gln Lys Ser Leu Ser Leu Ser Pro Gly Lys
         435                 440                 445
```

<210> SEQ ID NO 13
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="other DNA"
      /organism="Homo sapiens"

<400> SEQUENCE: 13

```
gcggccgcca tgaattttgg actgaggctg attttcctgg tgctgaccct gaaaggcgtc     60
cagtgtcagg tgcagctggt ccagtctgga gctgaggtga agaaaccagg agcctccgtg    120
aaggtctctt gcaaagccag tggcttcaac atcaaggaca catacatgta ttgggtgcga    180
caggcccctg gccagggtct ggaatggatg gcggcgtgg accccgcaaa tggaaatact    240
agatacgatc ctaaatttca aggcagggtg accctgacac gggacacttc aacctcgacg    300
gtctatatgg agctgtccag cctgagatcc gaagatacag cagtgtacta ttgtgggcgc    360
gacggtgcta tggactactg gggccaggga actctggtga ccgtctcgag cgctagcaca    420
aagggcccta gtgtgtttcc tctggctccc tcttccaaat ccacttctgg tggcactgct    480
gctctgggat gcctggtgaa ggattacttt cctgaacctg tgactgtctc atggaactct    540
ggtgctctga cttctggtgt ccacactttc cctgctgtgc tgcagtctag tggactgtac    600
tctctgtcat ctgtggtcac tgtgccctct tcatctctgg aacccagac ctacatttgt    660
aatgtgaacc acaaaccatc caacactaaa gtgacaaaa agtggaacc caaatcctgt    720
gacaaaaccc acacctgccc accttgtcct gcccctgaac tgctgggagg accttctgtg    780
tttctgttcc cccccaaacc aaaggatacc ctgatgatct ctagaacccc tgaggtgaca    840
tgtgtggtgg tggatgtgtc tcatgaggac cctgaggtca aattcaactg gtacgtggat    900
ggagtggaag tccacaatgc caaaaccaag cctagagagg aacagtacaa ttcaacctac    960
agagtggtca gtgtgctgac tgtgctgcat caggattggc tgaatggcaa ggaatacaag   1020
tgtaaagtct caaacaaggc cctgcctgct ccaattgaga aaacaatctc aaaggccaag   1080
ggacagccta gggaaccca ggtctacacc ctgccacctt caagagagga atgaccaaa   1140
aaccaggtgt ccctgacatg cctggtcaaa ggcttctacc cttctgacat tgctgtggag   1200
tgggagtcaa atggacagcc tgagaacaac tacaaaacaa ccccccctgt gctggattct   1260
gatggctctt ctttctgta ctccaaactg actgtggaca gtctagatg gcagcagggg   1320
aatgtctttt cttgctctgt catgcatgag gctctgcata accactacac tcagaaatcc   1380
ctgtctctgt ctcccgggaa atgatagtaa aagctt                             1416
```

<210> SEQ ID NO 14
<211> LENGTH: 445
<212> TYPE: PRT
<213> ORGANISM: Homo sapiens

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Gly Val Asp Pro Ala Asn Gly Asn Thr Arg Tyr Asp Pro Lys Phe
```

```
                50                  55                  60
Gln Gly Arg Val Thr Leu Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Gly Arg Asp Gly Ala Met Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 15
<211> LENGTH: 1416
<212> TYPE: DNA
<213> ORGANISM: Homo sapiens
```

<220> FEATURE:
<221> NAME/KEY: source
<222> LOCATION: 1..1416
<223> OTHER INFORMATION: /mol_type="other DNA"
      /organism="Homo sapiens"

<400> SEQUENCE: 15

```
gcggccgcca tgaattttgg actgaggctg attttcctgg tgctgaccct gaaaggcgtc      60
cagtgtcagg tgcagctggt ccagtctgga gctgaggtga agaaaccagg agcctccgtg     120
aaggtctctt gcacagctag tggcttcaac atcaaggaca cttacatgta ttgggtgaaa     180
caggcccctg ccagggtct ggaatggatt ggcggcgtgg accccgcaaa cgggaatacc      240
agatacgatc ctaagtttca aggcaaagcc accctgacaa gggacacttc aacctcgacg     300
gtgtatatgg agctgtccag cctgaggtcc gaagatacag cagtgtacta ttgtgggcgg     360
gacggtgcta tggactactg gggccaggga actctggtga ccgtctcgag cgctagcaca     420
aagggcccta gtgtgtttcc tctggctccc tcttccaaat ccacttctgg tggcactgct     480
gctctgggat gcctggtgaa ggattacttt cctgaacctg tgactgtctc atggaactct     540
ggtgctctga cttctggtgt ccacactttc cctgctgtgc tgcagtctag tggactgtac     600
tctctgtcat ctgtggtcac tgtgccctct tcatctctgg gaacccagac ctacatttgt     660
aatgtgaacc acaaaccatc caacactaaa gtggacaaaa agtggaaacc caaatcctgt     720
gacaaaaccc acacctgccc accttgtcct gcccctgaac tgctggggag accttctgtg     780
tttctgttcc cccccaaacc aaaggatacc ctgatgatct ctagaacccc tgaggtgaca     840
tgtgtggtgg tggatgtgtc tcatgaggac cctgaggtca aattcaactg gtacgtggat     900
ggagtggaag tccacaatgc caaaaccaag cctagagagg aacagtacaa ttcaacctac     960
agagtggtca gtgtgctgac tgtgctgcat caggattggc tgaatggcaa ggaatacaag    1020
tgtaaagtct caaacaaggc cctgcctgct ccaattgaga aaacaatctc aaaggccaag    1080
ggacagccta gggaacccca ggtctacacc ctgccacctt caagagagga atgaccaaa     1140
aaccaggtgt ccctgacatg cctggtcaaa ggcttctacc cttctgacat tgctgtggag    1200
tgggagtcaa atggacagcc tgagaacaac tacaaaacaa ccccccctgt gctggattct    1260
gatggctctt tctttctgta ctccaaactg actgtggaca gtctagatg gcagcagggg    1320
aatgtcttt  cttgctctgt catgcatgag gctctgcata accactacac tcagaaatcc    1380
ctgtctctgt ctcccgggaa atgatagtaa aagctt                              1416
```

<210> SEQ ID NO 16
<211> LENGTH: 445
<212> TYPE: PRT
<213> ORGANISM: Homo sapiens

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Met Tyr Trp Val Lys Gln Ala Pro Gly Gln Gly Leu Glu Trp Ile
        35                  40                  45

Gly Gly Val Asp Pro Ala Asn Gly Asn Thr Arg Tyr Asp Pro Lys Phe
    50                  55                  60

Gln Gly Lys Ala Thr Leu Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                    85                  90                  95

Gly Arg Asp Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 17
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="other DNA"
      /organism="Homo sapiens"
```

<400> SEQUENCE: 17

```
gcggccgcca tgaattttgg actgaggctg attttcctgg tgctgaccct gaaaggcgtc      60
cagtgtgagg tgcagctggt ccagagtggg gcagaagtga agaaaccagg tgccacagtg     120
aagatctcat gcaaagtctc cggcttcaac attaaggaca cttacatgta ttgggtgcag     180
caggcccccg gcaagggtct ggagtggatg ggcggcgtgg accccgctaa cggcaatacc     240
agatacgatc ctaagtttca aggacgggtg accatcacag ctgacactag caccgatacg     300
gcatatatgg agctgtccag cctgagatct gaagatacag cagtgtacta ttgtgccagg     360
gacgggggcta tggattactg gggccaggga actctggtga ccgtctcgag cgctagcaca     420
aagggcccta gtgtgtttcc tctggctccc tcttccaaat ccacttctgg tggcactgct     480
gctctgggat gcctggtgaa ggattacttt cctgaacctg tgactgtctc atggaactct     540
ggtgctctga cttctggtgt ccacactttc cctgctgtgc tgcagtctag tggactgtac     600
tctctgtcat ctgtggtcac tgtgccctct tcatctctgg aacccagac ctacatttgt     660
aatgtgaacc acaaaccatc aacactaaa gtggacaaaa agtggaacc caaatcctgt     720
gacaaaaccc acacctgccc accttgtcct gcccctgaac tgctgggagg accttctgtg     780
tttctgttcc ccccaaaacc aaaggatacc ctgatgatct ctagaacccc tgaggtgaca     840
tgtgtggtgg tggatgtgtc tcatgaggac cctgaggtca aattcaactg gtacgtggat     900
ggagtggaag tccacaatgc caaaaccaag cctagagagg aacagtacaa ttcaacctac     960
agagtggtca gtgtgctgac tgtgctgcat caggattggc tgaatggcaa ggaatacaag    1020
tgtaaagtct caaacaaggc cctgcctgct ccaattgaga aaacaatctc aaaggccaag    1080
ggacagccta gggaacccca ggtctacacc ctgccacctt caagagagga atgaccaaa    1140
aaccaggtgt ccctgacatg cctggtcaaa ggcttctacc cttctgacat tgctgtggag    1200
tgggagtcaa atggacagcc tgagaacaac tacaaaacaa ccccccctgt gctggattct    1260
gatggctctt tctttctgta ctccaaactg actgtggaca agtctagatg gcagcagggg    1320
aatgtctttt cttgctctgt catgcatgag gctctgcata accactacac tcagaaatcc    1380
ctgtctctgt ctcccgggaa atgatagtaa aagctt                              1416
```

<210> SEQ ID NO 18
<211> LENGTH: 445
<212> TYPE: PRT
<213> ORGANISM: Homo sapiens

<400> SEQUENCE: 18

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met Tyr Trp Val Gln Gln Ala Pro Gly Lys Gly Leu Glu Trp Met
        35                  40                  45

Gly Gly Val Asp Pro Ala Asn Gly Asn Thr Arg Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ala Met Asp Tyr Trp Gly Gln Gly Thr Leu Val Thr
            100                 105                 110
```

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 19
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="other DNA"
      /organism="Homo sapiens"

<400> SEQUENCE: 19
gcggccgcca tgaattttgg actgaggctg attttcctgg tgctgaccct gaaaggcgtc    60

-continued

```
cagtgtgaca tcgtgatgac acagtcacct gattccctgg cagtcagtct gggcgagaga    120
gccactatta actgcaagtc cagccagtct ctgctgtact ctagtaacca gaaaaattac    180
ctggcttggt atcagcagaa gccagggcag ccccctaaac tgctgatcta ttgggcaagc    240
accagggaat ctggagtgcc cgaccggttc agcggttctg gcagtggaac agattttacc    300
ctgacaattt catccctgca agccgaggac gtggctgtct actattgtca gcagtactat    360
acttacccac tgaccttcgg cggagggacc aagctcgaga tcaaacgtac ggtcgcggcg    420
ccttctgtgt tcattttccc cccatctgat gaacagctga atctggcac tgcttctgtg    480 gtctgtctgc tgaacaactt ctaccctaga gaggccaaag tccagtggaa agtggacaat    540
gctctgcaga gtgggaattc ccaggaatct gtcactgagc aggactctaa ggatagcaca    600
tactccctgt cctctactct gacactgagc aaggctgatt acgagaaaca caaagtgtac    660
gcctgtgaag tcacacatca ggggctgtct agtcctgtga ccaaatcctt caataggga    720 gagtgctgat agtaaaagct t                                              741
```

<210> SEQ ID NO 20
<211> LENGTH: 220
<212> TYPE: PRT
<213> ORGANISM: Homo sapiens

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 21
<211> LENGTH: 741
<212> TYPE: DNA
<213> ORGANISM: Homo sapiens

```
<220> FEATURE:
<221> NAME/KEY: source
<222> LOCATION: 1..741
<223> OTHER INFORMATION: /mol_type="other DNA"
      /organism="Homo sapiens"

<400> SEQUENCE: 21
gcggccgcca tgaattttgg actgaggctg attttcctgg tgctgaccct gaaaggcgtc    60
cagtgtgaca tcgtgatgac acagtcacct gattccctgg cagtcagtct gggcgagaga   120
gccactatta actgcaagtc cagccagtct ctgctgtact ctagtaacca gaaaaattat   180
ctggcttggc accagcagaa gccagggcag ccccctaaac tgctgatcta ctgggcaagc   240
accagggaat ctggagtgcc cgaccggttc agcggttctg gcagtggaac agattttacc   300
ctgacaattt catccctgca agccgaggac gtggctgtct actattgtca gcagtactat   360
acttatccac tgaccttcgg cggagggacc aagctcgaga tcaaacgtac ggtcgcggcg   420
ccttctgtgt tcattttccc cccatctgat gaacagctga atctggcac tgcttctgtg    480 gtctgtctgc tgaacaactt ctaccctaga gaggccaaag tccagtggaa agtggacaat   540
gctctgcaga gtgggaattc caggaatct gtcactgagc aggactctaa ggatagcaca    600
tactccctgt cctctactct gacactgagc aaggctgatt acgagaaaca caaagtgtac   660
gcctgtgaag tcacacatca ggggctgtct agtcctgtga ccaaatcctt caatagggga   720
gagtgctgat agtaaaagct t                                             741

<210> SEQ ID NO 22
<211> LENGTH: 220
<212> TYPE: PRT
<213> ORGANISM: Homo sapiens

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp His Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
              195                 200                 205
Ser Pro Val Thr Lys Ser Phe Asn Arg Gly Glu Cys
    210                 215                 220

<210> SEQ ID NO 23
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="other DNA"
      /organism="Homo sapiens"

<400> SEQUENCE: 23
gcggccgcca tgaattttgg actgaggctg attttcctgg tgctgaccct gaaaggcgtc      60
cagtgtgaca tcgtgatgac acagtcacct gattccctgg cagtctccct gggcgagaga     120
gccactatga gttgcaagtc cagccagtct ctgctgtact ctagtaacca gaaaaattat     180
ctggcttggc accagcagaa gccagggcag cccctaaac tgctgatcta ctgggcaagc      240
accagggaat ctggagtgcc cgaccggttc agcggttctg gcagtggaac agattttacc     300
ctgacaattt catccctgca agccgaggac gtggctgtct actattgtca gcagtactat     360
acttatccac tgaccttcgg cggagggacc aagctcgaga tcaagcgtac ggtcgcggcg     420
ccttctgtgt tcattttccc cccatctgat gaacagctga atctggcac tgcttctgtg      480 gtctgtctgc tgaacaactt ctaccctaga gaggccaaag tccagtggaa agtggacaat     540
gctctgcaga gtgggaattc ccaggaatct gtcactgagc aggactctaa ggatagcaca     600
tactccctgt cctctactct gacactgagc aaggctgatt acgagaaaca caaagtgtac     660
gcctgtgaag tcacacatca ggggctgtct agtcctgtga ccaaatcctt caatagggga     720
gagtgctgat agtaaaagct t                                               741

<210> SEQ ID NO 24
<211> LENGTH: 220
<212> TYPE: PRT
<213> ORGANISM: Homo sapiens

<400> SEQUENCE: 24

Asp Ile Val Met Thr Gln Ser Pro Asp Ser Leu Ala Val Ser Leu Gly
1               5                  10                  15

Glu Arg Ala Thr Met Ser Cys Lys Ser Ser Gln Ser Leu Leu Tyr Ser
            20                  25                  30

Ser Asn Gln Lys Asn Tyr Leu Ala Trp His Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 25
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="other DNA"
      /organism="Homo sapiens"

<400> SEQUENCE: 25
gcggccgcca tgaattttgg actgaggctg attttcctgg tgctgaccct gaaaggcgtc      60
cagtgtgaca tcgtgatgac acagtcacct gattccctgg cagtctccct gggcgagaga     120
gccactatga gttgcaagtc cagccagtct ctgctgtact ctagtaacca gaaaaattat     180
ctggcttggc accagcagaa gccaggacag ccccctaaac tgctgatcta ctgggcaagc     240
accagggaat ctggcgtgcc cgaccggttc agcggctctg gaagtgggac agattttacc     300
ctgacaatct catccctgca agccgaggac ctggctatct actattgtca gcagtactat     360
acttatccac tgaccttcgg tgccggcacc aagctcgaga tcaaacgtac ggtcgcggcg     420
ccttctgtgt tcattttccc cccatctgat gaacagctga atctggcac tgcttctgtg     480 gtctgtctgc tgaacaactt ctaccctaga gaggccaaag tccagtggaa agtggacaat     540
gctctgcaga gtgggaattc ccaggaatct gtcactgagc aggactctaa ggatagcaca     600 tactcccctgt cctctactct gacactgagc aaggctgatt acgagaaaca caaagtgtac     660
gcctgtgaag tcacacatca ggggctgtct agtcctgtga ccaaatcctt caatagggga     720
gagtgctgat agtaaaagct t                                                741

<210> SEQ ID NO 26
<211> LENGTH: 220
<212> TYPE: PRT
<213> ORGANISM: Homo sapiens

<400> SEQUENCE: 26

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Leu Tyr Ser
            20                  25                  30

Ser Asn Gln Lys Asn Tyr Leu Ala Trp His Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Ile Tyr Tyr Cys Gln Gln
                85                  90                  95
```

-continued

```
Tyr Tyr Thr Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

HUMANIZED ANTI-BAG3 ANTIBODIES

The present invention provides for a humanized anti-BAG3 antibody or a fragment thereof, pharmaceutical compositions comprising said antibody and its use as a medicament, in particular for use in the treatment of pancreatic tumours or other pathologies of an immune, inflammatory, neoplastic, cardiovascular and/or degenerative nature.

BACKGROUND OF THE INVENTION

BAG3 protein is a 74 kDa cytoplasmic protein which belongs to the family of co-chaperons that interact with the ATPase domain of the protein HSP70 (Heat Shock Protein) through the structural domain known as the BAG domain (amino acids 110-124). Furthermore, BAG3 protein contains a WW domain (Trp-Trp), a proline-rich region (PXXP), and two conserved motifs IPV (Ile-Pro-Val), which can mediate binding to other proteins. Thanks to the nature of BAG3 protein as an adapter, attributable to the presence of many functional domains, such protein can therefore interact with different proteins.

In humans, bag3 gene expression is constitutive for a few kinds of normal cells, including myocytes, while mutations thereof are associated with diseases of the skeletal and cardiac muscles. Furthermore, BAG3 protein is expressed in many types of primary tumours or tumour cell lines (lymphoid or myeloid leukemias, neuroblastoma, pancreatic cancer, thyroid cancer, breast cancer and prostate cancer, melanoma, osteosarcoma, glioblastoma and tumours of the kidney, colon, ovary, etc.) (Rosati A. et al., 2011).

In normal cell types, such as leukocytes, epithelial cells and glial cells and cells of the retina, bag3 gene expression can be induced by stressors, such as oxidants, high temperatures, lack of serum, heavy metals, HIV-1 infections, etc. These findings indicate that bag3 gene expression regulation is an important component in the cellular response to stress and is correlated with the presence of elements that respond to the transcription factor HSF1 (Heat Shock Transcription Factor), which is activated in various forms of cellular stress in bag3 gene promoter (Franceschelli S. et al., 2008).

Moreover, due to the presence of many protein-protein interaction domains in the structure thereof, BAG3 protein influences cell survival in different types of cells, interacting with different molecular partners. (Rosati A. et al., 2011). The first mechanism reported in relation to BAG3 anti-apoptotic activity was identified in osteosarcoma and melanoma cells, where it was observed that BAG3 protein modulates the activation of transcription factor NF-kB and cell survival (Ammirante M. et al., 2010). A different molecular mechanism has been described in glioblastoma cells, where BAG3 protein cooperates in a positive way with HSP70 protein to maintain BAX protein in the cytosol and prevent the translocation thereof into the mitochondria (Festa M. et al., 2011). Finally, in some tumours, BAG3 has been shown to regulate proteins that modulate cell adhesion.

The presence of cytoplasmic BAG3 protein has also been described in many different cellular systems and has been associated, not only with various tumours, but also in pathologies in general related to cell survival.

Furthermore, patent application n. WO2011/067377 describes extracellular BAG3 protein, secreted by some cell types, as a biochemical marker in serum, which is highly specific for the diagnosis of certain pathological conditions, such as cardiac pathologies and pancreatic tumour.

It has recently been reported that BAG3 protein is expressed in 346/346 patients with pancreatic ductal adenocarcinoma (PDAC) and is released by the cells of the pancreatic tumour, but such protein is not expressed in either the surrounding non-neoplastic tissues or in a normal pancreas; likewise, it has been reported that the levels of BAG3 expression are related to patient survival. The results of the study demonstrate that the use of specific siRNA molecules for BAG3 mRNA can silence bag3 gene expression and induce cell death, confirming that BAG3 protein is an important survival factor for pancreatic tumour cells and that the down-regulation thereof, when combined with gemcitabine, may contribute to the eradication of the tumor cells (Rosati A. et al., 2012).

Moreover, in a recent paper we have reported that PDAC-released BAG3 binds macrophages inducing their activation and the secretion of PDAC supporting factors. We have also identified IFITM-2 as a BAG3 receptor and showed that it signals through PI3K and the p38 MAPK pathways. Finally, we have showed that the use of a mouse monoclonal anti-BAG3 antibody results in reduced tumor growth and prevents metastasis formation in three different mouse models. We have therefore identified a paracrine loop involved in PDAC growth and metastatic spreading, and showed that an anti-BAG3 antibody has therapeutic potential (Rosati A. et al., Nat. Commun. 2015)

Conventional chemotherapy treatments for tumour pathologies, as well as treatments of inflammatory and immune diseases with corticosteroids or NSAIDs (non-steroidal anti-inflammatory drugs) pose numerous drawbacks linked to side effects and are not, at present, definitive means of treating such pathologies.

There is therefore an evident need for a new and improved therapeutic treatment which has the advantage of being highly specific and having few or no side effects, as compared with the conventional, commonly known therapies used for the treatment of diseases of an inflammatory, immune, and neoplastic nature described in the present invention.

Definitions

Unless otherwise defined, all terms of art, notations and other scientific terminology used herein are intended to have the meanings commonly understood by those persons skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "antibody" as used herein includes "fragments" or "derivatives", which have at least one antigen binding site of the antibody and/or show the same biological activity.

An antibody preferably comprises at least one heavy immunoglobulin chain and at least one light immunoglobulin chain. An immunoglobulin chain comprises a variable domain and optionally a constant domain. A variable domain may comprise complementarity determining regions (CDRs), e.g. a CDR1, CDR2 and/or CDR3 region, and framework regions.

The term "humanized antibody" refers to an antibody of human origin, whose hypervariable region has been replaced by the homologous region of non-human monoclonal antibodies.

The term "chimeric antibody" refers to an antibody containing portions derived from different antibodies.

The term "recombinant antibody" refers to an antibody obtained using recombinant DNA methods.

The term "scFv fragment" (single chain variable fragment) refers to immunoglobulin fragments only capable of binding with the antigen concerned. ScFv fragments can also be synthesised into dimers (diabodies), trimers (triabodies) and tetramers (tetrabodies) using peptide linkers.

The terms "Fab fragment" (antigen-binding fragment) and "Fab2 fragment" refer to immunoglobulin fragments consisting of a light chain linked to the Fc fragment of the adjacent heavy chain, and such fragments are monovalent antibodies. When the Fab portions are in pairs, the fragment is called Fab2.

The term "hybridoma" refers to a cell producing monoclonal antibodies.

The term "monospecific antibodies" refers to antibodies that all have affinity for the same antigen.

The term "multispecific antibodies" refers to antibodies that have affinity for several antigens.

The term "bispecific antibody" refers to an antibody that has affinity for two different antigens.

DESCRIPTION OF THE FIGURES

FIG. 1. ELISA showing the screening for antibody binding activity with a coating using Peptide 2 (BAG3 fragment).

FIG. 2. ELISA showing the screening for antibody binding activity with a coating using recombinant full length BAG3 protein.

FIG. 3. Flow cytometric evaluation of the ability of the antibody variants to block BAG3 binding to macrophage surface.

FIG. 4. Effect of humanized AC-2 antibody variants on tumor growth in vivo.

FIG. 5. Effect of humanized AC-2 antibody variant H2L4 on activated fibroblasts within the tumor mass.

FIG. 6. Quantification of the AC-2 H2L4 effect on activated fibroblasts number.

DISCLOSURE OF THE INVENTION

It has been surprisingly found by the inventors that specific BAG3 inhibitors are able to induce tumor regression. In particular, the humanized anti-BAG3 antibodies, tested showed a particular affinity for BAG3 protein and can be used in therapy as BAG3 inhibitors, as the block the interaction between BAG3 protein and its receptor on the macrophage surfaces.

Furthermore, the experimental data reported in the application demonstrates that said anti-BAG3 antibodies are particularly effective in reducing the activation of fibroblasts and therefore that they can be used in the treatment of all the pathologies wherein fibroblasts are highly activated, such as neoplastic diseases, inflammatory diseases, immune diseases and/or degenerative diseases.

Therefore, a first embodiment of the present invention relates to an antibody or fragment thereof which binds to the BAG3 protein and which comprises:
a) a heavy chain amino acid sequence as encoded by SEQ ID NO: 12 or at least the variable domain thereof or an amino acid sequence having a sequence identity of at least 80% thereof, and
b) a light chain amino acid sequence as encoded by SEQ ID NO: 20 or at least the variable domain thereof or an amino acid sequence having a sequence identity of at least 80% thereof.

As used herein, "sequence identity" between two polypeptide sequences, indicates the percentage of amino acids that are identical between the sequences, preferably over the entire length of the amino acid sequences as encoded by SEQ ID NO: 12 and SEQ ID NO: 20.

Preferred polypeptide sequences of the invention have a sequence identity of at least 85%, more preferably 90%, even more preferably 93%, 95%, 96%, 97%, 98% or 99%.

In a preferred embodiment of the present invention said amino acid sequence having a sequence identity of at least 80% with respect to SEQ ID N. 12 is selected from SEQ ID N. 14, SEQ ID N: 16 or SEQ ID N. 18.

In a further preferred embodiment said amino acid sequence having a sequence identity of at least 80% with respect to SEQ ID N. 20 is selected from SEQ ID N. 22, SEQ ID N: 24 or SEQ ID N. 26.

In a preferred embodiment the antibody of the present invention is the antibody wherein the heavy chain amino acid sequence is encoded by SEQ ID NO. 18 and the light chain amino acid sequence is encoded by SEQ ID NO 22 or SEQ ID N. 26.

In a preferred embodiment, the heavy chain amino acid sequence or at least the variable domain thereof or an amino acid sequence having a sequence identity of at least 80% thereof, comprises the CDRs regions having the following amino acid composition: H-CDR1 comprises the amino acids GFNIKDTYMY (SEQ ID N. 3), H-CDR2 comprises the amino acids GVDPANGNTRYDPKFQG (SEQ ID N. 4). H-CDR3 comprises the amino acids DGAMDY (SEQ ID N. 5) and the light chain amino acid sequence or at least the variable domain thereof or an amino acid sequence having a sequence identity of at least 80% thereof, comprises the CDRs regions having the following amino acid composition: L-CDR1 comprises the amino acids KSSQSLLYSSNQKNYLA (SEQ ID N. 6), L-CDR2 comprises the amino acids WASTRES (SEQ ID N. 7) and L-CDR3 comprises the amino acids QQYYTYPLT (SEQ ID N. 8).

A further embodiment of the present invention, is an antibody or a fragment thereof which binds to the BAG3 protein and which comprises:
a) a heavy chain nucleotide sequence as encoded by SEQ ID NO: 11 or at least the variable domain thereof or a nucleotide sequence having a sequence identity of at least 80% thereof, and
b) a light chain nucleotide sequence as encoded by SEQ ID NO: 19 or at least the variable domain thereof or a nucleotide sequence having a sequence identity of at least 80%0/ thereof.

As used herein, "sequence identity" between two nucleotide sequences, indicates the percentage of nucleotides that are identical between the sequences, preferably over the entire length of the nucleotide sequences as encoded by SEQ ID NO: 11 and SEQ ID NO: 19.

Preferred nucleotide sequences of the invention have a sequence identity of at least 85%, more preferably 90%, even more preferably 93%, 95%, 96%, 97%, 98% or 99%.

In a preferred embodiment of the present invention said nucleotide sequence having a sequence identity of at least 80% with respect to SEQ ID N. 11 is selected from SEQ ID N. 13, SEQ ID N: 15 or SEQ ID N. 17.

In a further preferred embodiment said amino acid sequence having a sequence identity of at least 80% with respect to SEQ ID N. 19 is selected from SEQ ID N. 21, SEQ ID N: 23 or SEQ ID N. 25.

In a preferred embodiment the antibody of the present invention is the antibody wherein the heavy chain amino acid sequence is encoded by SEQ ID NO. 17 and the light chain amino acid sequence is encoded by SEQ ID NO 21 or SEQ ID N. 25.

The antibody or fragments thereof according to the present invention may be any antibody of natural and/or synthetic origin, e.g. an antibody of mammalian origin. Preferably, the constant domain, if present, is a human constant domain. The variable domain is preferably a mammalian variable domain, e.g. a humanized or a human variable domain.

Antibodies or fragments thereof according to the invention may be polyclonal or monoclonal antibodies. Monoclonal antibodies are preferred. In particular the antibodies of the present invention are preferably selected from the group consisting of recombinant antibodies, humanized or fully human antibodies, chimeric antibodies, multispecific antibodies, in particular bispecific antibodies, or fragments thereof.

Monoclonal antibodies may be produced by any suitable method such as that of Köhler and Milstein (1975) or by recombinant DNA methods. Monoclonal antibodies may also be isolated from phage antibody libraries using techniques described in Clackson et al. (1991). Humanized forms of the antibodies may be generated according to the methods known in the art, (Kettleborough C. A. et al., 1991), such as chimerization or CDR grafting. Alternative methods for the production of humanized antibodies are well known in the art and are described in, e.g., EP 0239400 and WO 90/07861. Human antibodies can also be derived by in vitro methods. Suitable examples include but are not limited to phage display, yeast display, and the like.

According the present invention "chimeric antibody" relates to antibodies comprising polypeptides from different species, such as, for example, mouse and human. The production of chimeric antibodies is described, for example, in WO 89/09622.

The term antibody includes "fragments" or "derivatives", which have at least one antigen binding site of the antibody.

According to a preferred embodiment the antibody or fragment thereof may be a Fab fragment, a Fab' fragment, a F(ab') fragment, a Fv fragment, a diabody, a ScFv, a small modular immunopharmaceutical (SMIP), an affibody, an avimer, a nanobody, a domain antibody and/or single chains.

The antibody of the invention may be preferably of the IgG1, IgG2, IgG3, IgG4, IgM, IgA1, IgA2, IgAsec, IgD, and IgE antibody-type. It will be appreciated that antibodies that are generated need not initially possess such an isotype but, rather the antibody as generated can possess any isotype and that the antibody can be isotype-switched.

A further embodiment of the present invention is a vector comprising the nucleic acid coding for the antibody of the invention. Said vector is selected from a phage, a plasmid, a viral or a retroviral vector. Preferably, the vector of the invention is an expression vector wherein the nucleic acid molecule is operatively linked to one or more control sequences allowing the transcription and optionally the expression in prokatiotic and/or eukaryotic host cells.

A further embodiment of the present invention is a host comprising the vector of the invention, selected from a prokaryotic or eukaryotic cell, preferably a mammalian or a human cell, or a non-human transgenic animal.

A further embodiment of the present invention is a method for the preparation of the antibody or a fragment thereof disclosed above, comprising culturing the host of the invention under conditions that allow synthesis of said antibody and recovering said antibody from said culture.

A further embodiment is an antibody or a fragment thereof obtained by the method disclosed above.

Preferably, the antibodies of fragments thereof according to the present invention are humanized antibodies.

A further embodiment of the present invention is the use of the aforesaid antibody or a fragment thereof as medicament, preferably in the treatment of a particular pathological state which involves the activation of macrophages. Such pathological state can be chosen from: neoplastic diseases, inflammatory diseases, immune diseases or degenerative diseases.

Preferably, such neoplastic diseases may be either pancreatic tumour or bladder tumor, more preferably pancreatic tumour.

Preferably, said inflammatory diseases can be chosen from diseases related to inflammation of the skin, nerves, bones, blood vessels or connective tissues, and more preferably, psoriasis, arthritis, neuritis or connectivitis.

Preferably, said immune diseases can be chosen from autoimmune diseases such as rheumatic diseases, connective tissue diseases, neuromuscular diseases, endocrine diseases, gastrointestinal diseases, haematologic diseases, skin diseases or vasculitis, and more preferably, rheumatoid arthritis, multiple sclerosis, connectivitis, lupus erythematosus, endometriosis or ulcerative colitis.

Preferably, said degenerative diseases can be chosen from neurodegenerative diseases and muscular degenerative diseases, and more preferably Alzheimer's disease, Parkinson's disease, or muscular dystrophy.

A further aim of the present invention is a pharmaceutical composition comprising the aforesaid antibody or fragment thereof in association with at least one pharmaceutically acceptable excipient or carrier.

A further embodiment of the present invention is the use of said composition as a medicament.

A preferred embodiment of the present invention is the use of the composition in the treatment of neoplastic diseases and diseases of an inflammatory, immune and/or degenerative nature, preferably neoplastic disease, selected from pancreatic tumor or bladder tumor.

The composition of the present invention can be formulated in a form suitable for oral administration or in a form suitable for parenteral or topical administration.

In a preferred embodiment of the present invention, said oral form can be chosen from the following: tablets, capsules, solutions, suspensions, granules and oily capsules.

In a further preferred embodiment of the present invention, said topical form can be chosen from the following: cream, ointment, ointment, solution, suspension, eye drops, pessary, nebuliser solution, spray, powder, or gel.

In a further preferred embodiment of this invention, said parenteral form can be either an aqueous buffer solution or an oily suspension.

Said parenteral administration include administration by intramuscular, intravenous, intradermal, subcutaneous, intraperitoneal, intranodal, or intrasplenic means.

Preferably the pharmaceutical composition according the present invention comprises a further active principle, selected from antimetabolites, camptothecins or taxanes.

More preferably said active principles are selected from: Gemcitabine, 5-fluorouracil. Irinotecan, Oxaliplatin, Albumin-bound paclitaxel, Capecitabine, Cisplatin, Paclitaxel, Docetaxel or Irinotecan liposome.

EXAMPLES

Example 1—Chimerization and Humanization of AC2 Antibody

AC-2 murine antibody is produced by a hybridoma isolated from the hybridoma mother clone n° PD02009 deposited on the 17 Dec. 2002 at the Centro Biotecnologie Avanzate di Genova and disclosed in WO03/055908. Total RNA was extracted and RT-PCR performed to clone and sequence the variable regions of the antibody using conventional procedures (e.g., by using oligonucleotide probes that are capable of binding specifically to genes encoding the heavy and light chains of murine antibodies).

Based on sequence information of the variable region, heavy chain and light chain of AC-2 murine antibody (SEQ ID No. 1 and SEQ ID N. 2 for the amino acid sequences and SEQ ID 9 and SEQ ID N. 10 for the nucleotide sequences), different humanized variants of said region have been obtained by gene synthesis using standard procedures.

Sequences coding for the antibody variants were cloned in Evi-5 expression vector (Evitria AG, Switzerland) and expressed in CHO-K1 cells.

For antibody chimerization, the murine constant regions were replaced with the human constant regions. One chimeric versions of the heavy chain (HC) was made in an IgG1 context.

For antibody humanization, Complementarity Determining Regions (CDRs) from the murine were grafted into a human antibody framework.

Twenty four humanized versions of the heavy chain (HC) were made in an IgG1 and LC-kappa context. Each version is characterized by specific point mutations in the FR.

Example 2—Screening for Antibody Binding Activity

Chimeric Ab and humanized variants were tested in parallel for the ability to bind to BAG3, using an indirect ELISA test.

Material and Methods 96 well microplate (NUNC Maxisorp) were coated using a specific sequence (Pep2) within the BAG3 full-length protein (from aa 385 to aa 399) recognized by the murine antibody (AC-2). The plate was incubated overnight with 1 μg/ml of Pep2 (50 μl/well) in a phosphate buffer (PBS, pH 7.4). Then, the plate was washed two times with a detergent solution (0.05% Tween-20 in PBS), and the blocking of non-specific sites was performed for one hour at room temperature using, for each well, 150 μl of a solution of 0.5% fish gelatin (Sigma) in phosphate buffer (PBS, pH 7.4). Plates were washed two times with the washing buffer and then the antibodies were loaded on. In some of the wells, scalar dilutions of chimeric and humanized variants of the antibody, 500 ng/ml (50 μl/well) were loaded in duplicates. Antibodies were diluted in a solution of 0.5% fish gelatin, 0.05% Tween in PBS (BSA/Tween). The plate was incubated for 2 h at room temperature and then washed for 5 times with washing buffer. Samples were then incubated 30 minutes at room temperature with 50 μl/well of HRP-conjugated anti-mouse IgG or HRP-conjugated anti-human IgG as the secondary antibody. After 6 washes with the washing buffer, the peroxidase substrate, tetramethylbenzidine (TMB), was added to the wells (50 μl/well). The colorimetric reaction was blocked after 10 minutes by addition of sulfuric acid 0.5 M (25 μl/well) and the optic density values (OD) were detected using a spectrophotometer at the wavelength of 450 nm (FIG. 1). Chimeric and humanized variants of the antibody were tested also using plates coated with recombinant BAG3 full-length protein (rBAG3) by indirect ELISA test using the same protocol described above (FIG. 2).

Results

Binding of the different antibody variants was detected in ELISA using peptide 2 as coating (FIG. 1) or recombinant full length BAG3 (FIG. 2). The following antibody variants showed higher binding ability and were chosen for further analysis: H1L2, H1L3, H1L4, H2L2, H2L3, H2L4, H3L2, H3L3, H3L4, H4L2, H4L3, H4L4.

Example 3—Humanized Antibody Variants KD Determination

Materials and Methods

Binding experiments were performed on Octet Red96 at 25° C. Antibodies were captured on dip and read AHC (anti-human IgG Fc capture) sensors, followed by binding of Ag (*E. Coli* rBAG3) at variable concentrations. Binding of antigen to the antibodies was monitored in real time to obtain on (ka) and off (kd) rates. The equilibrium constant (KD) was calculated from the observed ka and kd.

Full kinetic analysis was performed using analyte concentrations from 100 nM to 0. The analysis was performed using analyte concentrations of 100 nM and run with serial dilutions in assay buffer, 100, 50, 25, 12.5, 6.25, 3.125, 1.56 and 0 nM. Chi square ($\chi^2$) analysis was carried out between the actual Sensorgram (colored line) and the sensorgram generated from the Fortebio Octet analysis software (red line) to determine the accuracy of the analysis. 2 value within 1-2 is considered significant (accurate) and below 1 is highly significant (highly accurate).

Note: 2×8 sensors were used for 1 full kinetic analysis, sensors were regenerated and used multiple times and captured with BAG-H-L, BAG-H1-L2, BAG-H1-L3, BAG-H1-L4, BAG-H2-L2, BAG-H2-L3, BAG-H2-L4, BAG-H3-L2, BAG-H3-L3, BAG-H3-L4, BAG-H4-L2, BAG-H4-L3, BAG H4-L4 to perform 13 full kinetics.

Results

Affinity for the different variants calculated as above is reported below. The AC-2 murine antibody showed a KD (M) of $10^{-12}$ while all human variants showed a KD (M) of $10^{-9}$ (see Table 1). However, this difference did not impact on variants biological activity as will be described.

TABLE 1

Affinity of AC-2 antibody variants

| Ligand | Analyte | ka (1/Ms) | kd (1/s) | KD (M) | e conc. In nM | Chi² |
|---|---|---|---|---|---|---|
| BAG-H-L | rBAG3 | $2.15 \times 10^5$ | $5.71 \times 10^{-4}$ | $2.66 \times 10^{-9}$ | 0-50 | 0.145 |
| BAG-H1-L2 | rBAG3 | $2.23 \times 10^5$ | $6.35 \times 10^{-4}$ | $2.84 \times 10^{-9}$ | 0-50 | 0.174 |
| BAG-H1-L3 | rBAG3 | $2.17 \times 10^5$ | $6.15 \times 10^{-4}$ | $2.83 \times 10^{-9}$ | 0-50 | 0.168 |
| BAG-H1-L4 | rBAG3 | $2.42 \times 10^5$ | $5.66 \times 10^{-4}$ | $2.34 \times 10^{-9}$ | 0-50 | 0.186 |
| BAG-H2-L2 | rBAG3 | $2.46 \times 10^5$ | $6.47 \times 10^{-4}$ | $2.63 \times 10^{-9}$ | 0-50 | 0.514 |
| BAG-H2-L3 | rBAG3 | $2.25 \times 10^5$ | $4.47 \times 10^{-4}$ | $1.98 \times 10^{-9}$ | 0-50 | 0.283 |
| BAG-H2-L4 | rBAG3 | $2.33 \times 10^5$ | $4.75 \times 10^{-4}$ | $2.04 \times 10^{-9}$ | 0-50 | 0.298 |
| BAG-H3-L2 | rBAG3 | $1.93 \times 10^5$ | $3.45 \times 10^{-4}$ | $1.78 \times 10^{-9}$ | 0-50 | 0.128 |
| BAG-H3-L3 | rBAG3 | $2.05 \times 10^5$ | $3.35 \times 10^{-4}$ | $1.61 \times 10^{-9}$ | 0-50 | 0.128 |
| BAG-H3-L4 | rBAG3 | $2.29 \times 10^5$ | $3.91 \times 10^{-4}$ | $1.70 \times 10^{-9}$ | 0-50 | 0.270 |
| BAG-H4-L2 | rBAG3 | $1.92 \times 10^5$ | $3.90 \times 10^{-4}$ | $2.02 \times 10^{-9}$ | 0-50 | 0.185 |
| BAG-H4-L3 | rBAG3 | $2.02 \times 10^5$ | $4.03 \times 10^{-4}$ | $1.98 \times 10^{-9}$ | 0-50 | 0.193 |
| BAG-H4-L4 | rBAG3 | $2.33 \times 10^5$ | $4.01 \times 10^{-4}$ | $1.72 \times 10^{-9}$ | 0-50 | 0.240 |

Example 4—Evaluation of the Ability of the Antibody Variants to Block BAG3 Binding to Macrophage Surface BAG3 binds to the surface of macrophages and we have showvn that binding is specifically inhibited by the murine anti-BAG AC-2 antibody that sequesters BAG3 protein.

Here we tested the ability of chimeric and humanized variants of the antibody to block binding to the macrophage surface.

Materials and Methods

J774 A.1 cells (1×106/ml) were incubated with blocking solution (PBS containing 5% FBS/0.1% NaN3) and with FcR blocking mouse (Miltenyi Biotec-cod. 130-092-575) (1 µl/1×106 cells) for 30 minutes at 4° C. Then, 1×105 cells were incubated with FITC-rBAG3 protein (40 µg/ml) alone or in presence of anti-BAG3 mouse antibody (AC2) (3200 µg/ml) or murine IgG1 (3200 µg/ml), or with the chimeric and humanized variants of the antibody (3200 µg/ml), or human IgG (3200 µg/ml) in blocking solution, for 30 minutes on ice. After incubation, cells were washed with PBS and analyzed by flow cytometry.

Results

Flow cytometric evaluation of fluorescent BAG3 binding to the surface of J774 A.1 macrophage cell line. Data are reported as mean fluorescence intensity (FIG. 3). On the basis of these results, the H4L2, H4L3, H4L4 and H2L4 humanized antibody variants were chosen.

Example 5—Evaluation of the Ability of Humanized AC-2 Antibody Variants to Block Primary Monocyte Activation The H4L2, H4L3, H4L4 and H2L4 humanized antibody variants were selected, purified by means of Protein A capture (HiTrap Protein A HP, GE Healthcare), and further tested for their ability block activation of primary human monocytes.

We have previously shown that BAG3 can activate primary human macrophages. Here we use IL6 secretion as a read out of macrophage activation to show the ability of the H4L2, H4L3, and H4L4 humanized antibody variants to block BAG3 dependent monocyte activation.

Materials and Methods

Buffy Coats (CompoFlex Triple "Top and Top" System-Fresenius Kabi) were obtained from healthy donors and stored overnight at 4° C. PBMC were isolated on standard Ficoll-Hypaque density gradients. Mononuclear cells were isolated and subjected to sequential washes with 50 ml of PBS 1× in order to eliminate platelets and erythrocytes contaminations: (I: at 1100 g for 20 mins; II: at 800 g for 10 mins; III: at 400 g for 10 mins; IV: at 300 g for 10 mins; V and VI: at 100 g for 10 mins). All centrifugations were made with the brake off. Cells were then checked under the microscope and if contaminations were still present, an additional centrifugation at 100 g for 10 mins was performed.

PBMC were then plated in 96 well microplates (2×10$^6$ cells/ml) and cultured in RPMI without glutamine (100 µl/well) without FBS and with FcR Blocking Reagent human (1 µl every 1 million of cells) (Miltenyi 130-059-901) for 16 hours (overnight).

The day after, cells were treated for 6 h with rBAG3 (0.5 µg/ml). mAb blocking assays were performed incubating the rBAG3 together with different concentrations of AC-2 or the humanized variants.

Treatment was performed without changing the media to the cells, but adding 100 µl of RPMI without FBS to each well containing molecules described above. All molecules were added to 100 µl of RPMI without FBS in a sterile tube and molecules were added at twice of their final concentration to the cells. Molecules were pre-incubated for 30 minutes at room temperature in the tubes and then added to the cells. Pre-incubation is necessary for mAb blocking assays. After treatment cell culture medium was collected after centrifugation at 400 g for 5 minutes. Surnatants were analyzed for IL-6 contents in duplicate at 1:10 dilution with a human ELISA IL-6 Kit (eBioscience, San Diego, Calif.). IL-6 concentration were evaluated by comparing the OD of the sample with that of a standard curve of recombinant IL-6.

Results

Results reported in Table 2 are expressed as % of inhibition of IL-6 production induced by rBAG3 by the different antibodies. All variants show inhibitory ability comparable to the murine AC2 anti BAG3 antibody. H4L2 and H4L4 were chosen for further testing in vivo, for their ability block tumor growth in a xenograft tumor model.

TABLE 2

| % inhibition of BAG3 dependent IL6 secretion | | |
| --- | --- | --- |
| AC2 120x | AC2 60x | AC2 30x |
| 85.9% | 53.4% | 13.1% |
| 74.4% | 31.8% | 18.6% |
| H4L2 120x | H4L260x | H4L2 30x |
| 80.3% | 47.4% | 14.2% |
| 71.0% | 27.4% | 2.0% |
| H4L3 120x | H4L3 60x | H4L3 30x |
| 80.4% | 51.2% | 25.9% |
| 73.2% | 42.3% | 20.4% |
| H4L4 120x | H4L4 60x | H4L4 30x |
| 84.3% | 46.4% | 3.15% |
| 75.0% | 41.2% | 7.7% |
| H2L4 120x | H2L4 60x | H2L4 30x |
| 83.0% | 52.0% | 2.14% |
| 73.7% | 53.2% | 25.9% |
| B12 120x | B12 60x | B12 30x |
| 1.3% | 0.7% | 3.2% |
| 0.1% | 3.1% | 0.7% |

Example 6—Effect of Humanized AC-2 Antibody Variants on Tumor Growth In Vivo

Based on in vitro experiments we choose variant H4L2 and H2L4 for the subsequent in vivo validation.

Materials and Methods

Mia-Paca 2 cells (2×10$^6$) were suspended in PBS (200 µl) and injected into the right flank of female CD1 mice (6 weeks old; Charles River, Italy). After 10 days mice were divided in four arms consisting of 7 (control) or 6 (treated) mice each in which tumor volume average ranged 80-100 mm3. Control group received vehicle (PBS) i.p. injection every 48 hrs whilst treated groups received i.p. injection every 48 hrs of murine (AC2) or humanized H2L4, H4L2 anti-BAG3 mAbs at the dose of 20 mg/kg in PBS for 5 weeks. Animals were weighted and tumor volume measured by caliper ($Dxd^2/2$) once weekly.

Results

FIG. 4 reports tumor fold change at week intervals of control (PBS) or animals treated with the indicated antibodies. The ratio is between the average volume at the indicated time point and the average volume at day 0. While tumors of control treated animals show a 4 fold increase, treated animals only increase by 2.5 fold.

Example 7—Impact of Humanized AC-2 H2L4 Variant on Activated Fibroblast Number within the Tumor Mass Results obtained on tumor growth prompted us to further investigate changes in tumor microenvironment. One of the major player in tumor development are fibroblasts associated to the tumor mass.

Materials and Methods

At the end of the experiment described in example 6 tumors were paraffin embedded and sections analysed by immunofluorescence using an anti-α sma antibody (A2547, Sigma-Aldrich, at 1:350). Nuclei were counterstained with 1 µg ml$^{-1}$ Hoechst 33342 (Molecular Probes, Oregon, USA). Images were acquired in sequential scan mode by using the same acquisitions parameters (laser intensities, gain photomultipliers, pinhole aperture, objective×40, zoom 1) when comparing experimental and control material. Leica Confocal Software and ImageJ were used for data analysis (% of α-sma positive area).

Results

FIG. 5 show representative images from 2 PBS-treated and 2 AC-2 H2L4 treated tumors of α-sma staining. The presence of activated fibroblasts associated to the masses grown in the control animals is very high as demonstrated by α-sma protein positivity. Instead, AC-2 H2L4 treated animals are negative. In FIG. 6 we have reported a quantification of α-sma positive area by comparing control (PBS-treated) and AC-2 H2L4 treated samples.

These data strongly support the evidence that humanized anti-BAG3 antibodies have an effect on fibroblasts that have an important role not only in neoplastic diseases but also in other pathological processes such as inflammation (Kalluri, 2016).

REFERENCES

Ammirante M, Rosati A, Arra C, Basile A, Falco A, Festa M, Pascale M, d'Avenia M, Marzullo L, Belisario M A, De Marco M, Barbieri A. Giudice A, Chiappetta G, Vuttariello E, Monaco M, Bonelli P. Salvatore G, Di Benedetto M, Deshmane S L, Khalili K, Turco M C, Leone A. "IKK{gamma} protein is a target of BAG3 regulatory activity in human tumor growth". Proc Natl Acad Sci USA. 2010:107(16):7497-502.

Clackson T, Hoogenboom H R Griffiths A D, Winter G. Making antibody fragments using phage display libraries. Nature 1991; 15; 352(6336):624-8.

Festa M, Del Valle L, Khalili K, Franco R, Scognamiglio G, Graziano V, De Laurenzi V, Turco M C, Rosati A. "BAG3 protein is overexpressed in human glioblastoma and is a potential target for therapy". Am J Pathol. 2011; 178(6): 2504-12.

Franceschelli S, Rosati A, Lerose R, De Nicola S, Turco M C, Pascale M. "Bag3 gene expression is regulated by heat shock factor 1". J Cell Physiol. 2008; 215(3):575-7.

Kalluri R. The biology and function of fibroblasts in cancer. Nature Reviews Cancer. 2016; 16, 582-598

Kettleborough C A, Saldanha J, Heath V J, Morrison C J, Bendig M M. "Humanization of a mouse monoclonal antibody by CDR-grafting: the importance of framework residues on loop conformation". Protein Eng. 1991; 4(7): 773-83.

Kohler G, Milstein C. Continuous cultures of fused cells secreting antibody of predefined specificity. Nature 1975; 256:495-497.

Rosati A, Graziano V, De Laurenzi V, Pascale M, Turco M C. "BAG3: a multifaceted protein that regulates major cell pathways". Cell Death Dis. 2011 Apr. 7; 2:e141.

Rosati A, Bersani S. Tavano F, Dalla Pozza E, De Marco M. Palmieri M, De Laurenzi V, Franco R, Scognamiglio G, Palaia R, Fontana A, di Sebastiano P, Donadelli M, Dando I, Medema J P, Dijk F, Welling L, di Mola F F, Pezzilli R, Turco M C, Scarpa A. "Expression of the antiapoptotic protein BAG3 is a feature of pancreatic adenocarcinoma and its overexpression is associated with poorer survival". Am J Pathol. 2012 November; 181(5): 1524-9.

Rosati A, Basile A, D'Auria R, d'Avenia M, De Marco M, Falco A. Festa M, Guerriero L, Iorio V, Parente R, Pascale M, Marzullo L, Franco R, Arra C, Barbieri A, Rea D, Menichini G, Hahne M, Bijlsma M, Barcaroli D, Sala G, di Mola F F, di Sebastiano P, Todoric J, Antonucci L, Corvest V, Jawhari A, Firpo M A, Tuveson D A, Capunzo M, Karin M, De Laurenzi V, Turco M C. "BAG3 promotes pancreatic ductal adenocarcinoma growth by activating stromal macrophages". Nat Commun., 6:8695 doi: 10, 1038/ncomms9695.

The invention claimed is:

1. A humanized antibody or a fragment thereof that binds to BAG3 protein and comprises:
   a) a heavy chain comprising the following CDRs: H-CDR1 comprising the amino acids GFNIKDTYMY (SEQ ID NO: 3), H-CDR2 comprising the amino acids GVDPANGNTRYDPKFQG (SEQ ID NO: 4), H-CDR3 comprising the amino acids DGAMDY (SEQ ID NO: 5), and
   b) a light chain comprising the following CDRs: L-CDR1 comprising the amino acids KSSQSLLYSSNQK-NYLA (SEQ ID NO: 6), L-CDR2 comprising the amino acids WASTRES (SEQ ID NO: 7) and L-CDR3 comprising the amino acids QQYYTYPLT (SEQ ID NO: 8).

2. The humanized antibody or a fragment thereof according to claim 1, characterized in that the heavy chain comprises an amino acid sequence is selected from SEQ ID NO: 14, SEQ ID NO: 16 or SEQ ID NO: 18.

3. The humanized antibody or a fragment thereof according to claim 1, characterized in that the light chain comprises an amino acid sequence is selected from SEQ ID NO: 22, SEQ ID NO: 24 or SEQ ID NO: 26.

4. The humanized antibody or a fragment thereof according to claim 1, characterized in that the heavy chain comprises SEQ ID NO:12 or at least the variable domain thereof or an amino acid sequence having a sequence identity of at least 80% thereof, and the light chain comprises SEQ ID NO:20 or at least the variable domain thereof or an amino acid sequence having a sequence identity of at least 80% thereof.

5. The humanized antibody or a fragment thereof according to claim 1, characterized in that the heavy chain amino acid sequence comprises SEQ ID NO: 18 and the light chain amino acid sequence comprises SEQ ID No: 22.

6. The humanized antibody or a fragment thereof according to claim 1, characterized in that it is an antibody of mammalian origin.

7. The humanized antibody or fragment thereof according to claim 1, characterized in that said antibody is a Fab fragment, a Fab' fragment, a F(ab') fragment, a Fv fragment, a diabody, a ScFv, a small modular immunopharmaceutical (SMIP), an affibody, an avimer, a nanobody, a domain antibody and/or single chains.

8. A nucleic acid encoding the antibody or a fragment thereof according to claim 1.

9. A vector comprising the nucleic acid according to claim 8.

10. A host cell comprising the nucleic acid of claim 8.

11. A method for treating a pathological state which involves the activation of macrophages, selected from neoplastic diseases, inflammatory diseases, immune diseases and/or degenerative diseases, comprising the step of administering the humanized antibody or a fragment thereof according to claim 1 to a subject in need thereof.

12. The method according to claim 11, wherein the method is for treating pancreatic tumour or bladder tumour.

13. A pharmaceutical composition comprising at least one antibody or a fragment thereof according to claim 1 and at least one pharmaceutically acceptable excipient or carrier.

14. The pharmaceutical composition according to claim 13 characterized in that said composition is formulated in a form suitable for oral administration or in a form suitable for parenteral or topical administration.

15. The pharmaceutical composition according to claim 13 characterized in that said composition comprises a further active principle, selected from antimetabolites, camptothecins or taxanes.

16. The humanized antibody or a fragment thereof according to claim 1, characterized in that the heavy chain amino acid sequence comprises SEQ ID NO: 18 and the light chain amino acid sequence comprises SEQ ID NO: 26.

17. A nucleic acid encoding the antibody or a fragment thereof according to claim 5.

18. A nucleic acid encoding the antibody or a fragment thereof according to claim 16.

19. A pharmaceutical composition comprising the antibody or a fragment thereof according to claim 5 and at least one pharmaceutically acceptable excipient or carrier.

20. A pharmaceutical composition comprising the antibody or a fragment thereof according to claim 16 and at least one pharmaceutically acceptable excipient or carrier.

* * * * *